(12) United States Patent
Soucaille et al.

(10) Patent No.: US 8,900,838 B2
(45) Date of Patent: Dec. 2, 2014

(54) METHOD FOR THE PREPARATION OF 1,3-PROPANEDIOL FROM SUCROSE

(75) Inventors: Philippe Soucaille, Deyme (FR); Cedric Boisart, Gerzat (FR)

(73) Assignee: Metabolic Exployer, Saint Beauzire (FR)

( * ) Notice: Subject to any disclaimer, the term of this patent is extended or adjusted under 35 U.S.C. 154(b) by 0 days.

(21) Appl. No.: 13/808,251

(22) PCT Filed: Jul. 5, 2011

(86) PCT No.: PCT/EP2011/061285
§ 371 (c)(1),
(2), (4) Date: Jan. 3, 2013

(87) PCT Pub. No.: WO2012/004247
PCT Pub. Date: Jan. 12, 2012

(65) Prior Publication Data
US 2013/0309737 A1  Nov. 21, 2013

Related U.S. Application Data

(60) Provisional application No. 61/361,455, filed on Jul. 5, 2010.

(30) Foreign Application Priority Data

Jul. 5, 2010   (EP) .................................... 10305729

(51) Int. Cl.
| | | |
|---|---|---|
| *C12P 7/18* | (2006.01) | |
| *C12N 1/21* | (2006.01) | |
| *C12N 9/04* | (2006.01) | |
| *C12N 9/10* | (2006.01) | |
| *C12N 9/88* | (2006.01) | |
| *C12N 15/52* | (2006.01) | |
| *C12N 1/20* | (2006.01) | |

(52) U.S. Cl.
CPC ............ *C12P 7/18* (2013.01); *C12Y 401/01001* (2013.01); *C12Y 101/01021* (2013.01); *C12N 9/1096* (2013.01); *C12Y 206/01052* (2013.01); *Y02E 50/17* (2013.01); *C12N 15/52* (2013.01); *C12N 1/20* (2013.01)
USPC ........... 435/158; 435/232; 435/190; 435/193; 435/252.33

(58) Field of Classification Search
None
See application file for complete search history.

(56) References Cited

U.S. PATENT DOCUMENTS

| | | |
|---|---|---|
| 7,745,195 B2 | 6/2010 | Chateau et al. |
| 8,088,620 B2 | 1/2012 | Bestel-Corre et al. |
| 8,168,434 B2 | 5/2012 | Soucaille et al. |
| 8,236,994 B2 | 8/2012 | Soucaille |
| 8,252,579 B2 | 8/2012 | Meynial-Salles et al. |
| 2005/0054060 A1 | 3/2005 | Chateau et al. |
| 2006/0270013 A1 | 11/2006 | Chateau et al. |
| 2007/0072279 A1 | 3/2007 | Meynial-Salles et al. |
| 2007/0087403 A1 | 4/2007 | Bestel-Corre et al. |
| 2008/0085558 A1 | 4/2008 | Soucaille et al. |
| 2008/0233617 A1 | 9/2008 | Figge et al. |
| 2008/0286840 A1 | 11/2008 | Figge et al. |
| 2008/0311632 A1 | 12/2008 | Figge et al. |
| 2009/0029424 A1 | 1/2009 | Bestel-Corre et al. |
| 2009/0081746 A1 * | 3/2009 | Liao et al. ..................... 435/160 |
| 2009/0155867 A1 | 6/2009 | Soucaille |
| 2009/0325245 A1 | 12/2009 | Soucaille et al. |
| 2010/0086982 A1 | 4/2010 | Soucaille |
| 2010/0137655 A1 | 6/2010 | Soucaille |
| 2010/0151536 A1 * | 6/2010 | Baynes et al. ................ 435/128 |
| 2010/0261240 A1 | 10/2010 | Ollivier |
| 2011/0257441 A1 | 10/2011 | Rousseaux et al. |
| 2011/0294178 A1 | 12/2011 | Soucaille et al. |
| 2012/0058531 A1 | 3/2012 | Chateau et al. |
| 2012/0190116 A1 | 7/2012 | Soucaille et al. |

FOREIGN PATENT DOCUMENTS

| | | |
|---|---|---|
| EP | 1149911 A2 | 10/2001 |
| WO | 9635796 A1 | 11/1996 |
| WO | 2004076659 A2 | 9/2004 |
| WO | 2004101479 A2 | 11/2004 |
| WO | 2005047498 A1 | 5/2005 |
| WO | 2005073364 A2 | 8/2005 |
| WO | 2005111202 A1 | 11/2005 |
| WO | 2006082252 A2 | 8/2006 |
| WO | 2006082254 A2 | 8/2006 |
| WO | 2007017710 A1 | 2/2007 |

(Continued)

OTHER PUBLICATIONS

Nakamura et al., Metabolic engineering for the microbial production of 1,3-propanediol, Curr. Opin. Biotech., 2003, 14, 454-59.*

(Continued)

*Primary Examiner* — Rebecca Prouty
*Assistant Examiner* — Todd M Epstein
(74) *Attorney, Agent, or Firm* — Miles & Stockbridge P.C.

(57) ABSTRACT

A microorganism genetically modified for the bioproduction of 1,3-propanediol from sucrose, wherein the microorganism includes:
   a two-step metabolic pathway for the production of 1,3-propanediol, including a first step of decarboxylation of 4-hydroxy-2-ketobutyrate with an enzyme having a 2-keto acid decarboxylase activity, and a second step of reduction of the obtained 3-hydroxypropionaldehyde with an enzyme having hydroxy aldehyde reductase activity, and
   genes enabling the microorganism to utilize sucrose as sole carbon source.

A method for the biological preparation of 1,3-propanediol by fermentation, including cultivating said microorganism genetically modified, wherein the culture is performed in an appropriate medium including a source of sucrose, and recovering the 1,3-propanediol being produced.

5 Claims, 1 Drawing Sheet

(56) References Cited

FOREIGN PATENT DOCUMENTS

| | | | |
|---|---|---|---|
| WO | 2007077041 A1 | 7/2007 | |
| WO | 2007085398 A2 | 8/2007 | |
| WO | 2007095255 A2 | 8/2007 | |
| WO | 2007141316 A2 | 12/2007 | |
| WO | 2007144346 A1 | 12/2007 | |
| WO | 2008040387 A1 | 4/2008 | |
| WO | 2008052595 A1 | 5/2008 | |
| WO | 2008052973 A2 | 5/2008 | |
| WO | 2009068110 A1 | 6/2009 | |
| WO | 2010037843 A1 | 4/2010 | |
| WO | 2010076324 A1 | 7/2010 | |
| WO | 2010128070 A2 | 11/2010 | |

OTHER PUBLICATIONS

Batista et al., Sucrose fermentation by *Saccharomyces cerevisiae* lacking hexose transport, J. Mol. Microbiol. Biotechnol., 2004, 8, 26-33.*

Shukla et al., Production of D(-)-lactate from sucrose and molasses, Biotechnol. Lett., 2004, 26, 689-693.*

Dickinson et al., The activity of yeast ADH I and ADH II with long-chain alcohols and diols, Chemico-Biological Inter., 2001, 130-132, 417-423.*

Frank et al., Crystal structure of the E1 Component of the *Escherichia coli* 2-Oxoglutarate Dehydrogenase Multienzyme Complex, J. Mol. Bio., 2007, 368, 639-51.*

Schmid et al, "Plasmid-Mediated Sucrose Metabolism in *Eucherichia coli* K12:Mapping of the SCR Genes of pUR400," Molecular Microbiology, vol. 2, No. 1, pp. 1-8, (1988).

Schmid et al., "Plasmid-Mediated Uptake and Metabolism of Sucrose by *Escherichia coli* K-12," Journal of Bacteriology, vol. 151, No. 1, pp. 68-76, (Jul. 1982).

Bockmann, "Characterization of a Chromosomally Encoded, Non-PTS Metabolic Pathway For Sucrose Utilization in *Escherichia coli* EC3132," Mol. Gen. Genet. vol. 235, pp. 22-32, (1992).

Jahreis, et al., "Adaption of Sucrose Metabolism in the *Escherichia coli* Wild-Type Strain EC3132," vol. 184, No. 19, pp. 5307-5316, (Oct. 2002).

Tsunekawa et al., "Acquisition of a Sucrose Utilization System in *Escherichia coli* K-12 Derivatives and Its Application to Industry," Applied and Environmental Microbiology, vol. 58, No. 6, pp. 2081-2088, (Jun. 22, 1992).

Penfold et al., "Production of H2 From Sucrose by *Escherichia coli* Strains Carrying the pUR400 Plasmid, Which Encodes Invertase Activity," Biotechnology Letters, vol. 26, pp. 1879-1883, (2004).

Anderson, "Growth Requirements of Virus-Resistant Mutants of *Escherichia coli* Strain "B"," Proc. Natl. Acad. Sci. vol. 32, pp. 120-128, (1946).

Schaefer et al., "Automated Sampling Device for Montoring Intracellular Metabolite Dynamics," Analytical Biochemistry, vol. 270, pp. 88-96, (1999).

Datsenko et al., One-Step Inactivation of Chromosomal Genes in *Escherichia coli* K-12 Using PCR Products, PNAS, vol. 97, No. 12, pp. 6640-6645 (Jun. 6, 2000).

Kovach et al., "Four New Derivatives of the Broad-Host-Range Cloning Vector pBBR1MCS, Carrying Different Antibiotic-Resistance Cassettes," Gene, vol. 166, pp. 175-176, (1995).

Harrington et al., "Balance Branching in Transcription Termination," PNAS, vol. 98, No. 9, pp. 5019-5024, (Apr. 24, 2001).

European Search Report for EP 10 30 5729, Search Completed on Sep. 17, 2010.

International Search Report for PCT/EP2011/061285 Mailed Sep. 15, 2011.

Steven M. Autieri et al., "L-Fucose Stimulates Utilization of D-Ribose by *Escherichia coli* MG1655 Δ fucAO and *E. coli* Nissle 1917 ΔfucAO Mutants in the Mouse Intestine and in M9 Minimal Medium." Infection and Immunity, American Society of Microbiology, 2007, vol. 75, No. 11, pp. 5465-5475.

J. Richard Dickinson et al, "The Catabolism of Amino Acids to Long Chain and Complex Alcohols in *Saccharomyces cerevisiae*," The Journal of Biological Chemistry, The American Society for Biochemistry and Molecular Biology, Inc., 2003, vol. 278, No. 10, pp. 8028-8034.

Birgit Geueke et al, "A New bacterial L-acid oxidase with a broad substrate specificity: purification and characterization," Enzyme and Microbial Technology, 2002, vol. 31, pp. 77-87.

Sandra Jeudy, "Crystal Structure of *Escherichia coli* DkgA, a Broad-Specificity Aldo-Keto Reductase," PROTEINS: Structure, Function, and Bioinformatics, 2006, vol. 62, pp. 302-307.

Roger S. Lane, "2-Keto-4-hydroxybutyrate Aldolase. Identification as 2-Keto-4-hydroxyglutarate Aldose, Catalytic Properties, and Role in the Mammalian Metabolism of L-Homoserine," Biochemistry, 1971, vol. 10, No. 8, pp. 1353-1364.

José Manuel Pérez, "*Escherichia coli* YqhD Exhibits Aldehyde Reductase Activity and Protects from the Harmful Effect of Lipid Peroxidation-derived Aldehydes," The Journal of Biological Chemistry, 2008, vol. 283, No. 12, pp. 7346-7353.

Marta De La Plaza et al., "Biochemical and molecular characterization of α-ketoisovalerate decarboxylase, an enzyme involved in the formation of aldehydes from amino acids by *Lactococcus lactis*," FEMS Microbiology Letters, 2004, vol. 238, pp. 367-374.

Dongyi Xu et al., "Methylglyoxal detoxification by an aldo-keto reductase in the cyanobacterium *Synechococcus* sp. PCC 7002," Microbiology, 2006, vol. 152, pp. 2013-2021.

\* cited by examiner

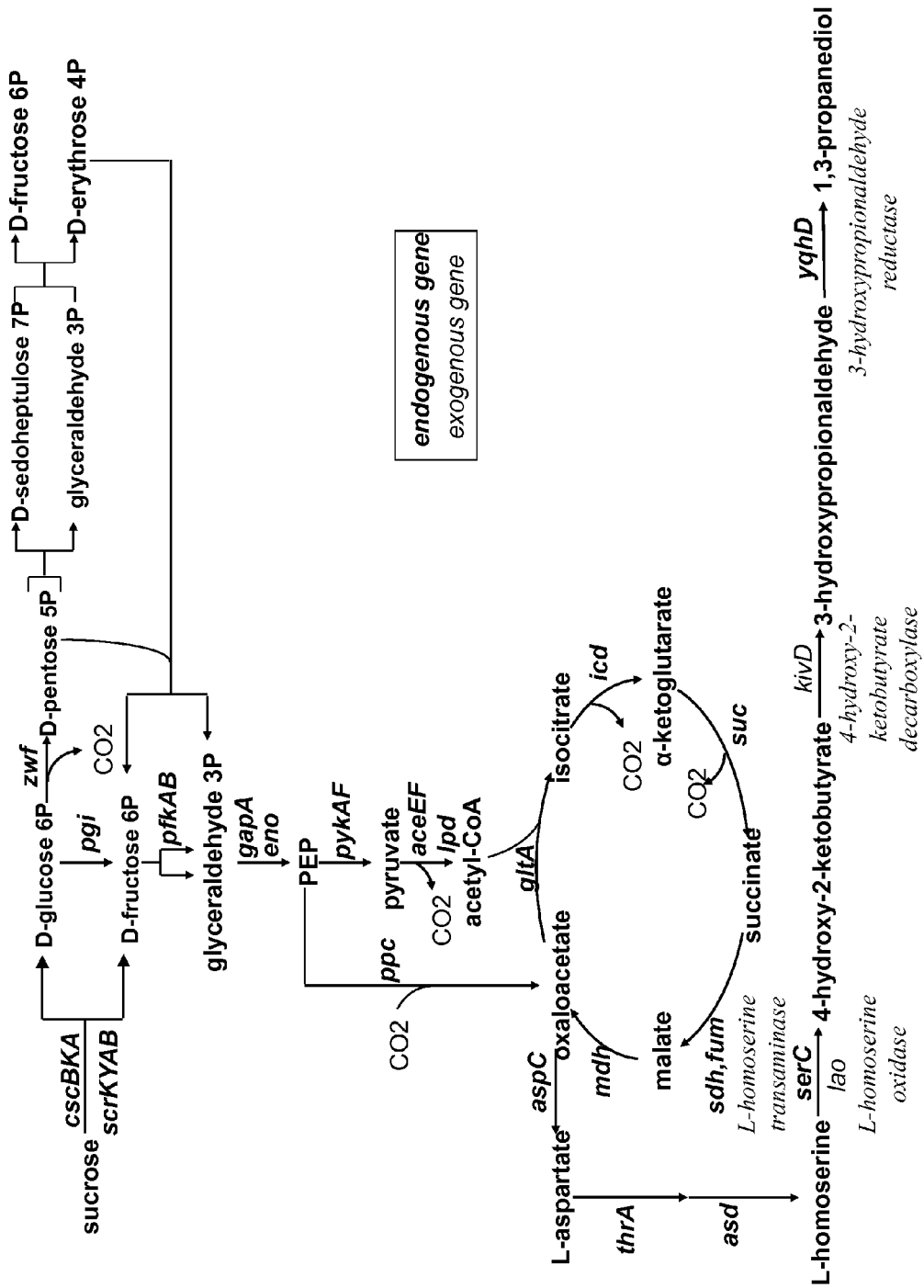

METHOD FOR THE PREPARATION OF 1,3-PROPANEDIOL FROM SUCROSE

CROSS REFERENCE TO RELATED APPLICATIONS

This application is a §371 National Stage Application of PCT/EP2011/061285, filed Jul. 5, 2011, which claims priority to European Application No. 10305729.5, filed Jul. 5, 2010 and U.S. Provisional Application No. 61/361,455, filed Jul. 5, 2010.

BACKGROUND OF THE INVENTION

1. Field of the Invention

The present invention concerns a new method for the biological preparation of 1,3-propanediol from sucrose, comprising culturing a microorganism genetically modified for the bioproduction of 1,3-propanediol, wherein the microorganism comprises a two-step metabolic pathway for the production of 1,3-propanediol from 4-hydroxy-2-ketobutyrate, comprising a first step of decarboxylation and a second step of reduction, and wherein said microorganism has been modified to be able to use sucrose as sole carbon source.

2. Description of Related Art

Fermentative production of 1,3-propanediol by culturing microorganism producing 1,3-propanediol is known in the art. Methods of production of 1,3-propanediol involving vitamin B12-dependent enzymes have already been described; these methods make the production process very expensive.

There is an ongoing need for alternative solutions to produce 1,3-propanediol with vitamin B12-independent pathway, from renewable sources of carbon. Moreover, there is an ongoing need for the improvement of the overall yield of product being produced, based on the necessary energy for such production. Finally, there is an ongoing need for controlling the level of impurities and by-products, for isolation of the product and its marketing and further use.

1,3-propanediol is mainly produced from glycerol (see the patent application PCT/EP2010/056078) and from glucose via the intermediate glycerol. Since the mondial glycerol stock is limited, there is a need to find other carbohydrates sources.

Carbon sources used in fermentation media generally consist in carbohydrates, mostly derived from plants. Starch is the most abundant storage carbohydrate in plants.

As the cost of the biotechnologically produced commodity chemicals is mainly related to the cost of raw material (i.e. the cost of the fermentation substrate), use of refined sugars is not an economically sustainable choice for industrial scale production. Less expensive substrates are needed that retain a high content of fermentable sugar. In this respect, sucrose coming from the sugar industry represents a good option.

Sucrose is obtained from sugar plants such as sugar beet, sugarcane, sweet sorghum, sugar maple, sugar palms or blue agaves. The different sucrose containing intermediates, products or by-products from the sugar processes (raw juice, thin or clarified juice, thick juice, sucrose syrup, pure sucrose, molasse) may serve as fermentation feedstock.

Two different systems for the uptake and utilization of sucrose in microorganisms have been characterized.

The first one is based on a phosphoenolpyruvate (PEP)-dependent sucrose phosphotransferase system (sucrose PTS) where sucrose is taken up and phosphorylated using phosphoenolpyruvate (PEP) as a donor to yield intracellular sucrose-6-phosphate. Sucrose-6-phosphate is then hydrolysed to D-glucose-6-phosphate and D-fructose by an invertase. D-fructose is further phosphorylated to D-fructose-6-phosphate by an ATP-dependent fructokinase and can then enter the central metabolism. Such a system has been described in several bacterial species, gram-positive as well as gram-negative. Among the Enterobacteriaceae family, more than 90% of wild-type *Klebsiella* but less than 50% of *Escherichia* and less than 10% of *Salmonella* strains are sucrose positive.

A conjugative plasmid pUR400 bearing the genes scrKY-ABR coding for the sucrose PTS has been isolated from *Salmonella* (Schmid et al., 1982, Schmid et al., 1988).

A second system called "non-PTS system" was discovered more recently in *E. coli* EC3132 (Bockmann et al., 1992). This system involves the genes cscBKAR coding for a sucrose:proton symport transport system (CscB), a fructokinase (CscK), an invertase (CscA) and a sucrose-specific repressor (CscR).

*Escherichia coli* K12 and its derivatives cannot utilize sucrose. However, this ability can be conferred by the transfer of the genes coding for the two previously described systems. This has been demonstrated by transferring the plasmid pUR400 in *E. coli* K12 (Schmid et al, 1982) or different plasmids (including pKJL101-1) bearing the cscBKAR genes in a sucrose negative strain of *E. coli* (Jahreis et al., 2002). As for industrial application, tryptophan production from sucrose has been documented in *E. coli* K12 (Tsunekawa et al., 1992), hydrogen production was shown in *E. coli* carrying the pUR400 plasmid (Penfold and Macaskie, 2004) and production of different amino-acids by transferring both systems, PTS and non-PTS was reported in patent application EP1149911.

Surprisingly, by combining genetic modifications leading to a sucrose utilization in *E. coli* strains unable to utilize sucrose, and a specific biosynthetic pathway for 1,3-propanediol, the inventors of the present invention were able to obtain improved yield of 1,3-propanediol production from a renewable source of carbon, sucrose.

SUMMARY

The present invention concerns a microorganism genetically modified for the bioproduction of 1,3-propanediol from sucrose, wherein the microorganism comprises:
  a two-step metabolic pathway for the production of 1,3-propanediol, comprising a first step of decarboxylation of 4-hydroxy-2-ketobutyrate with an enzyme having a 2-keto acid decarboxylase activity, and a second step of reduction of the obtained 3-hydroxypropionaldehyde with an enzyme having hydroxy aldehyde reductase activity, and
  genes enabling the microorganism to utilize sucrose as sole carbon source.

According to the invention, the microorganism contains at least one gene encoding a polypeptide with 2-keto acid decarboxylase activity and one gene encoding a polypeptide with hydroxy aldehyde reductase activity. Those genes can be exogenous or endogenous, and can be expressed chromosomally or extrachromosomally.

The microorganism according to the invention is furthermore genetically modified to be able to use sucrose as sole carbon source.

BRIEF DESCRIPTION OF THE DRAWINGS

FIG. 1 represents an embodiment as described herein.

DETAILED DESCRIPTION OF A PREFERRED EMBODIMENT

As used herein the following terms may be used for interpretation of the claims and specification.

The term 'sucrose' designates a disaccharide of glucose and fructose linked by a α(1,2) glycosidic bond, with the molecular formula $C_{12}H_{22}O_{11}$. Its systematic name is α-D-glucopyranosyl-(1→2)-β-D-fructofuranoside.

The term "genetically modified microorganism" means that the microorganism of the invention is not found in nature, and is modified either by introduction or by deletion of new genetic elements. It can also be transformed by forcing the development and evolution of new metabolic pathways in combining directed mutagenesis and evolution under specific selection pressure (see for instance WO 2004/076659).

A microorganism can express exogenous genes if these genes are introduced into the microorganism with all the elements allowing their expression in the host microorganism. Transforming microorganisms with exogenous DNA is a routine task for the man skilled in the art.

Exogenous genes can be integrated into the host genome, or be expressed extrachromosomally by plasmids or vectors. Different types of plasmids are known by the man skilled in the art, which differ with respect to their origin of replication and their copy number in the cell.

In specific embodiments, endogenous genes can also be modified to modulate their expression and/or activity, by introducing either mutations in the coding sequence to modify the gene product or by introducing heterologous sequences in addition or in replacement of the endogenous regulatory elements. Modulation of an endogenous gene can go both ways: upregulating and/or enhancing the activity of the gene product on the one hand, or down regulating and/or lowering the activity of the endogenous gene product on the other hand.

Important elements for controlling the expression of genes are promoters. In a preferred embodiment of the invention, genes may be expressed using promoters with different strength, which may be inducible. These promoters may be homologous or heterologous. The man skilled in the art knows how to choose the promoters that are the most convenient, for example promoters Ptrc, Ptac, Plac or the lambda promoter a are widely used.

According to the invention, 'an enzyme having a 2-keto acid decarboxylase activity' designates an enzyme having a decarboxylase activity, whose substrate is a 2-keto acid. Genes coding for a 2-keto acid decarboxylase activity are well known in the art, including Pdc genes from various species, and more particularly the Pdc1, Pdc5, Pdc6, Aro10 and Thi3 genes from *Saccharomyces cerevisiae*, kivD gene from *Lactococcus lactis*; pdc gene from *Clostridium acetobutylicum*; Pdc2 and Pdc3 genes from *Arabidopsis thaliana*; Pdc1, Pdc2 and Aro10 genes from *Pichia stipitis*; and pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*. Functional homologues, functional variants and functional fragments of said genes and proteins are encompassed by the definition.

According to the invention, 'an enzyme having a hydroxy aldehyde reductase activity' designates an enzyme having a reductase activity, whose substrate is a hydroxy aldehyde. Genes coding for a hydroxy aldehyde reductase activity are well known in the art, including the yqhD, fucO, dkgA, dkgB genes from *Escherichia coli* and the ADH1 and ADH2 genes from *Saccharomyces cerevisiae*. Functional homologues, functional variants and functional fragments of said genes and proteins are encompassed by the definition.

The term 'to utilize sucrose as sole carbon source' indicates that the microorganism can grow in a medium containing sucrose as unique carbon source. It is however understood that in the method for producing 1,3-propanediol according to the invention, the sucrose source in the culture medium can comprise additional carbon sources in addition to sucrose such as hexoses (such as glucose, galactose or lactose), pentoses, monosaccharides, disaccharides (such as sucrose, cellobiose or maltose), oligosaccharides, starch or its derivatives, hemicelluloses, glycerol and combinations thereof.

In a specific embodiment of the invention, the microorganism comprises functional genes coding for a PTS sucrose utilization system and/or for a non-PTS sucrose utilization system.

A PTS sucrose utilization system is a system for sucrose utilization based on the transport of sucrose by a phosphoenolpyruvate (PEP)-dependent sucrose phosphotransferase system (Sucrose-PTS). A phosphotransferase system couples the transport of a sugar (e.g. sucrose or glucose) with the phosphorylation of the sugar using PEP as phosphate donor. After transport into the cell, the sucrose-phosphate is cleaved into glucose-6-phosphate and fructose by an invertase. Fructose is then phosphorylated into fructose-6-phosphate by a fructokinase. The genes coding for this PTS sucrose utilization system can be controlled by a regulatory protein.

A non-PTS sucrose utilization system is a system for sucrose utilization based on transport of sucrose by a system independent of phosphoenolpyruvate. After transport into the cell, the sucrose is cleaved into glucose and fructose by an invertase. Fructose is then phosphorylated into fructose-6-phosphate by a fructokinase and glucose is phosphorylated into glucose-6-phosphate by a glucokinase. The genes coding for this non-PTS sucrose utilization system can be controlled by a regulatory protein.

In a specific aspect of the invention, the microorganism expresses naturally or has been modified with the introduction of the genes: scrKYABR (scrK coding for a fructokinase, scrY coding for a porin, scrA coding for the Protein IIBC, scrB coding for a sucrose-6-P invertase, scrR coding for a repressor) from *Salmonella*. A conjugative plasmid pUR400 bearing said genes scrKYABR might be used to transform the microorganism. These genes can be used all together in combination, or in any combination comprising at least one of these genes. In particular, the gene scrR can be omitted.

In another specific aspect of the invention, the microorganism expresses naturally or has been modified with the introduction of the genes from *E. coli* EC3132 i.e. the genes cscBKAR coding for a sucrose:proton symport transport system (cscB), a fructokinase (cscK), an invertase (cscA) and a sucrose-specific repressor (cscR). These genes can be used all together in combination or in any combination comprising at least one of these genes. In particular, the gene cscR can be omitted. Homologous genes from other organisms can also be used.

The designation of these genes has a more general meaning according to the invention, and covers the corresponding genes in other micro-organisms. Using the GenBank references of the genes from *Salmonella* or from *E. coli*, those skilled in the art can determine equivalent genes in organisms other than *Salmonella* or *E. coli*.

The means of identification of the homologous sequences and their percentage homologies are well-known to those skilled in the art, and include in particular the BLAST programmes that can be used on the website www.ncbi.nlm.nih.gov/BLAST/ with the default parameters indicated on that website. The sequences obtained can be exploited (aligned) using for example the programmes CLUSTALW (www.ebi.ac.uk/clustalw/), with the default parameters indicated on these websites.

The PFAM database (protein families database of alignments and hidden Markov models www.sangerac.uk/Software/Pfam/) is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins www.ncbi.nlm.nih.gov/COG/) are obtained by comparing protein sequences derived from 66 fully sequenced unicellular genomes representing 14 major phylogenetic lines. Each COG is defined from at least three lines, making it possible to identify ancient conserved domains.

Several techniques are currently used by the man skilled in the art for introducing DNA into a bacterial strain. A preferred technique is electroporation, which is well known to those skilled in the art.

According to a specific embodiment of the invention, the microorganism comprises an endogenous gene coding for a 2-keto acid decarboxylase activity. Said microorganism is preferably selected among *Saccharomyces cerevisiae* (comprising the genes Pdc1, Pdc5, Pdc6, Aro10, Thi3); *Lactococcus lactis* (Kivd); *Clostridium acetobutylicum* (Pdc); *Pichia stipitis* (Pdc1, Pdc2, Aro10); *Zymomonas mobilis* (Pdc); *Mycobacterium tuberculosis*.

In a preferred embodiment of the invention, the expression of the endogenous gene coding for the 2-keto acid decarboxylase is enhanced in said microorganism.

According to another embodiment of the invention, the microorganism does not comprise an endogenous gene coding for a 2-keto acid decarboxylase. Such microorganism lacking endogenous 2-keto acid decarboxylase is preferably selected among *Escherichia coli* or *Corynebacterium glutamicum* or *Bacillus subtilis*. For such microorganisms, the microorganism of the invention comprises a heterologous gene coding for a 2-keto acid decarboxylase. Genes coding for a 2-keto acid decarboxylase activity include Pdc genes from various species, and more particularly the Pdc1, Pdc5, Pdc6, Aro10 and Thi3 genes from *Saccharomyces cerevisiae*, kivD gene from *Lactococcus lactis*; pdc gene from *Clostridium acetobutylicum*; Pdc2 and Pdc3 genes from *Arabidopsis thaliana*; Pdc1, Pdc2 and Aro10 genes from *Pichia stipitis*; and pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*.

According to another embodiment of the invention, the microorganism comprises an endogenous gene coding for a hydroxy aldehyde reductase activity. It is preferably selected among *Escherichia coli* (yqhD, fucO, dkgA, dkgB); *Saccharomyces cerevisiae* (ADH1, ADH2); and all organisms having at least one enzyme having aldehyde reductase activity or alcohol dehydrogenase activity. This microorganism having endogenous hydroxy aldehyde reductase activity can be further modified to enhance expression of the endogenous gene coding for the hydroxy aldehyde reductase.

In a specific embodiment, the microorganism comprises an heterologous gene coding for a hydroxy aldehyde reductase activity. Genes coding for a hydroxy aldehyde reductase activity include the yqhD, fucO, dkgA, dkgB genes from *Escherichia coli* and the ADH1 and ADH2 genes from *Saccharomyces cerevisiae*.

According to another embodiment of the invention, the microorganism has been genetically modified for the improved production of 4-hydroxy-2-ketobutyrate from sucrose. This result can be achieved by increasing the expression of homoserine transaminase or homoserine oxidase. These enzymes allow conversion of L-homoserine (obtained from L-aspartate) into 4-hydroxy-2-ketobutyrate. Increasing the expression of homoserine oxidase can be accomplished by introducing and overexpressing the gene coding for L-amino acid oxidase from *R. opacus*, or by introducing mutations into the gene that increase the activity of the corresponding protein. Increasing the level of expression of homoserine transaminase can be accomplished by introducing artificial promoters that drive the expression of the serC gene of *E. coli*, by increasing the number of copies in the cell or by introducing mutations into the serC gene that increase the activity of the corresponding protein.

The global biosynthesis pathway of 1,3-propanediol is represented in FIG. 1.

In another embodiment, the microorganism presents a stimulated flux in the oxaloacetate biosynthesis pathway; this result can be achieved by increasing the level of expression of the phosphoenolpyruvate carboxylase, encoded by the ppc gene. Increasing the level of expression of the phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Increase of the oxaloacetate pool can also be achieved by increasing the level of expression of the exogenous pyruvate carboxylase, encoded by the pyc gene of *Rhizobium etli* or *Corynebacterium glutamicum*. Increasing the level of expression of the pyruvate carboxylase can be accomplished by overexpressing these genes, chromosomally or extrachromosomally. Specifically in anaerobic conditions, increase of the oxaloacetate pool can also be achieved by increasing the level of expression of the phosphoenolpyruvate carboxykinase, encoded by the pckA gene. Increasing the level of expression of the pyruvate carboxylase can be accomplished by introducing artificial promoters that drive the expression of the pckA gene, by increasing the number of copies in the cell or by introducing mutations into the pckA gene that increase the activity of the corresponding protein. Availability of the intermediate product oxaloacetate can also be increased by attenuating the level of expression of genes coding for phosphoenolpyruvate carboxykinase and/or malic enzymes, encoded by the pckA and/or sfcA or maeB genes, respectively. This can be done by replacing the wild-type promoter of these genes by a lower strength promoter, or by use of an element destabilizing the corresponding messenger RNA or the protein. If needed, complete attenuation of the genes can also be achieved by a deletion of the corresponding DNA sequences.

In another embodiment, the microorganism presents a stimulated flux into the homoserine biosynthesis pathway. This can be achieved by increasing the expression of aspartokinase and homoserine dehydrogenase and/or aspartate semialdehyde dehydrogenase, encoded by the thrA/metL and asd genes, respectively. Increasing the expression of aspartokinase and homoserine dehydrogenase and/or aspartate semialdehyde dehydrogenase can be accomplished by introducing artificial promoters that drive the expression of the thrA/metL and/or asd genes, by increasing the number of copies in the cell or by introducing mutations into the thrA and/or asd genes that increase the activity of the corresponding proteins.

In a particular embodiment of the invention, mutations can be introduced into the thrA gene that reduce its sensitivity to the feed-back inhibitor threonine (feed-back desensitized alleles) and thus permit an increased activity in the presence of threonine.

In a further embodiment of the invention, the microorganism is modified to present an attenuated level of homoserine conversion to other compounds than 1,3-propanediol. This result may be achieved by attenuating the level of homoserine consuming enzymes like homoserine kinase and threonine synthase (encoded by thrB and thrC), homoserine O-transsuccinylase (encoded by metA). These genes can be attenuated by replacing the natural promoter by a weaker promoter or by elements destabilizing the corresponding messenger RNA or protein. If needed, complete attenuation of the gene can also be achieved by the deletion of the corresponding DNA sequence.

In a further embodiment of the invention, the bacterium is modified to present an attenuated level of homoserine precursors conversion to other compounds than 3-hydroxypropionate; this result may be achieved by attenuating the level of dihydrodipicolinate synthase (encoded by dapA). Attenuation of this gene can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the microorganism is modified to present an attenuated level of 3-hydroxypropionaldehyde conversion to other compounds than 1,3-propanediol. This may be achieved by attenuating the level of 3-hydroxypropionaldehyde consuming enzymes like 3-hydroxypropionaldehyde dehydrogenase (encoded by aldA, aldB, aldH). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence.

All techniques for transforming the microorganisms, and regulatory elements used for enhancing production of the protein of the invention are well known in the art and available in the literature, including applicant's own patent applications on modification of biosynthesis pathways in various microorganisms, including WO 2008/052973, WO 2008/052595, WO 2008/040387, WO 2007/144346, WO 2007/141316, WO 2007/077041, WO 2007/017710, WO 2006/082254, WO 2006/082252, WO 2005/111202, WO 2005/073364, WO 2005/047498, WO 2004/076659, the content of which is incorporated herein by reference.

As previously described, the designation of these genes has a more general meaning according to the invention, and covers the corresponding genes in other micro-organisms.

According to the invention, the term "microorganism" designates a bacterium, yeast or a fungus. Preferentially, the microorganism is selected among Enterobacteriaceae, Clostridiaceae, Bacillaceae, Streptomycetaceae and Corynebacteriaceae. More preferentially the microorganism is a species of *Escherichia*, *Clostridium*, *Bacillus*, *Klebsiella*, *Pantoea*, *Salmonella* or *Corynebacterium*. Even more preferentially the microorganism is either the species *Escherichia coli* or *Corynebacterium glutamicum* or *Clostridium acetobutylicum* or *Bacillus subtilis*.

The present invention also concerns a method for the fermentative production of 1,3-propanediol from sucrose, comprising the steps of:
culturing a microorganism according to the invention on an appropriate culture medium comprising sucrose and recovering 1,3-propanediol from the culture medium.

The fermentation is generally conducted in fermenters with an appropriate culture medium adapted to the microorganism, containing sucrose, and if necessary co-substrates.

An 'appropriate culture medium' designates a medium (e.g., a sterile, liquid media) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like.

As an example of known culture mediums for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

The culture conditions for the fermentation process can be readily defined by those skilled in the art. In particular, bacteria are fermented at temperatures between 20° C. and 55° C., preferably between 25° C. and 40° C., and preferably at about 35° C. for Clostridiaceae and at about 37° C. for Enterobacteriaceae.

According to the invention the terms 'cultivating', 'culture', 'growth' and 'fermentation' are used interchangeably to denote the growth of bacteria in an appropriate growth medium containing a simple carbon source. Fermentation is a classical process that can be performed under aerobic, microaerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. Advantages of the fermentation under aerobic conditions instead of anaerobic conditions are that the presence of oxygen as an electron acceptor improves the capacity of the strain to produce more energy in form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

In a specific aspect of the invention, the sucrose is obtained from biomass, in particular from plant biomass. The whole plant or any specific part of a plant can be used to prepare the raw material used as sucrose-containing medium. The preparation can be based on any treatment known by those skilled in the art to extract sucrose from a sucrose-containing plant biomass.

In a preferred aspect of the invention, the sucrose-containing medium is obtained from a plant chosen among the group consisting of: sugarcane, sugar beet, sweet sorghum, sugar maple, sugar palm and blue agave.

Preferentially, the sucrose-containing medium is obtained from sugarcane or sugar beet.

Different forms of sucrose-containing medium can be used: a juice, a concentrated juice, a syrup, a clarified juice, molasses or crystallized sucrose. A preferred form is the raw juice from sugar cane, directly extracted from the plant without any treatment. Briefly, the harvested sugar cane is cleaned before the milling process for extraction of the juice. The structure of the cane is broken and then grinded, and at the same time the sucrose is extracted with water to get the raw juice. The raw juice may then be clarified by adding lime and heating and the clarified juice is separated from the precipitate. Concentrated syrup is obtained by evaporation.

As some crude sucrose-containing media, particularly those obtained from biomass as mentioned above, contain other nutrients that can be used for growth of microorganisms in addition to the sucrose-containing medium, an appropriate medium for the growth of microorganisms can be designed either by using the sucrose-containing medium alone, i.e. the appropriate medium consists of the sucrose-containing medium, or by complementing the sucrose-containing medium with a source of phosphorus and/or a source of nitrogen.

Preferentially, the sucrose-containing medium comprises at least 7% of sucrose.

In one aspect of the invention, the recovered 1,3-propanediol is furthermore purified. Recovering 1,3-propanediol from the culture medium is a routine task for a man skilled in the art. Methods for recovery and purification are disclosed in the following patent applications: WO 2009/068110 and WO 2010/037843.

Before describing the present invention in detail, it is to be understood that this invention is not limited to particularly exemplified methods and may, of course, vary. In particular, examples show modified *Escherichia coli* strains, but these modifications can easily be performed on other microorganisms of the same family.

*Escherichia coli* belongs to the Enterobacteriaceae family, that comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *Escherichia coli* (*E. coli*) is one of the most important model organisms, but we can also cite as important members of the Enterobacteriaceae family: *Klebsiella*, in particular *Klebsiella pneumoniae*, and *Salmonella*.

DRAWINGS

FIG. 1. Biosynthesis pathway of the 1,3-propanediol from sucrose.

Example 1

Calculation of Maximum Yields for 1,3-propanediol Production on Glucose and Sucrose 1.1—Parameters Used for Simulations Simulations were performed with the METEX proprietary software METOPT™. A simplified metabolic network of *E. coli* was used including a central metabolic network, metabolic pathways for all biomass precursors and specific production pathways as described above. A classical biomass composition for *E. coli* was used. Simulations were performed using either glucose or sucrose carbon source. For sucrose utilization, both the PTS system and the non-PTS system were modelled. As there were no differences on maximal yields calculated, only one yield on sucrose is reported. Calculation of a practical maximum yield was performed, taking into account a growth rate of 0.1 $h^{-1}$ and maintenance energy of 5 $mmol_{ATP} \cdot g_{DW}^{-1} \cdot h^{-1}$. All simulations were performed with a specific uptake rate of glucose of 3 $mmol \cdot g_{DW}^{-1} \cdot h^{-1}$. Simulations were performed under aerobic conditions.

1.2–Simulation Results

|  | 1,3-propanediol on glucose | 1,3-propanediol on sucrose |
|---|---|---|
| Maximum practical yield (g/g) | 0.38 | 0.41 |

Example 2

Demonstration of the L-homoserine Transaminase Activity Encoded by the Gene serC of *Escherichia coli*

2.1—Construction of Strain for SerC Characterisation: BL21 (pPAL7-serC)

To characterise the SerC protein, the corresponding gene was expressed from the expression vector pPAL7 (Bio-rad).

For this purpose, the serC gene was amplified from the *E. coli* genome using the oligonucleotides pPAL7-serC F and pPAL7-serC R. The PCR product was restricted using enzymes HindIII and EcoRI and cloned into the vector pPAL7 restricted by the same restriction enzymes. The resulting vector was named pPAL7-serC.

pPAL7-serC F (SEQ ID NO 1): ccc AAGCTTtgATGGCTCAAATCTTCAATTTTAGTTC TGG
with
a region (bold case) homologous to the sequence (956876-956904) of the gene serC (reference sequence on the website www.ecogene.org/),
a region (underlined case) harbouring the HindIII restriction site pPAL7-serC R (SEQ ID NO 2): g GAATTCTTAACCGTGACGGCGTTCGAACTCAACC
with
a region (bold case) homologous to the sequence (957964-957937) of the gene serC region (reference sequence on the website www.ecogene.org/),
a region (underlined case) harbouring the EcoRI restriction site.

The pPAL7-serC plasmid was then introduced into competent BL21 (DE3) cells (Invitrogen).

2.2—Overproduction of the Protein SerC

The overproduction of the protein SerC was done in a 2 l Erlenmeyer flask, using LB broth (Bertani, 1951, J. Bacteriol. 62:293-300) that was supplemented with 2.5 g/l glucose and 100 mg/l of ampicillin. A preculture was grown overnight in a 500 ml Erlenmeyer flask filled with 50 ml of LB broth that was supplemented with 2.5 g/l glucose and 100 mg/l of ampicillin. The preculture was used to inoculate a 500 ml culture to an $OD_{600\,nm}$ of about 0.15. The culture was first grown at 37° C. and 200 rpm until the $OD_{600\,nm}$ was about 0.5 and then shifted to 25° C. and 200 rpm and grown until the $OD_{600\,nm}$ was 0.6-0.8 (about one hour), before induction with 500 μM IPTG. The culture was kept at 25° C. and 200 rpm until $OD_{600\,nm}$ was around 4, and then stopped. Cells were centrifuged at 7000 rpm for 5 minutes at 4° C., and then stored at −20° C.

2.3—Purification of the Protein SerC

2.3.1—Step 1: Preparation of Cell-Free Extracts

About 280 mg of *E. coli* biomass was suspended in 45 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris was removed by centrifugation at 12000 g for 30 min at 4° C.

2.3.2—Step 2: Affinity Purification

The protein was purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated 30 min with 100 mM potassium phosphate pH 7.6, 100 mM fluoride at room temperature. The protein was eluted from the column with 2 column volumes of 100 mM potassium phosphate pH 7.6. The tag remained tightly bound to the resin and the purified protein was released. The fractions containing the protein were pooled and dialyzed against 100 mM Tris HCl, 150 mM NaCl and 10% glycerol pH 8.

Protein concentration was measured using the Bradford protein assay.

2.4—L-homoserine Transaminase Assay

The L-homoserine transaminase activity was measured at 30° C. using a coupled enzymatic assay. The L-homoserine transaminase activity assay was carried out with 420 mM potassium phosphate buffer pH 8.2, 2 mM acetylpyridine adenine dinucleotide, 3 mM L-homoserine, 20 units/ml glutamic dehydrogenase from bovine liver, 1 mM alpha-ketoglutaric acid neutralized and about 50 μg of crude extract in a total volume of 1 ml. The consumption of acetylpyridine adenine dinucleotide was monitored at 375 nm on a spectrophotometer. The activity detected in control assay, lacking the substrate (L-homoserine), was subtracted from the activity detected in the assay with substrate. A unit of L-homoserine transaminase activity is the amount of enzyme required to catalyze the transamination of 1 μmol of L-homoserine per min at 30° C. (Epsilon 375 nm=6100 M-1 cm−1)

2.5—Activity of Purified Enzyme

|  | Activity of purified enzyme (mUI/mg) |
|---|---|
| L-Homoserine transaminase assay | 118 |

Example 3

Demonstration of the 4-hydroxy-2-ketobutyrate decarboxylase Activity Encoded by the Gene kivD of *Lactococcus lactis*

3.1—Construction of Strain for KivD Characterisation: BL21 (pPAL7-kivDll)

To characterise the KivD protein, the corresponding gene was expressed from the expression vector pPAL7 (Bio-rad).

For this purpose, the kivD gene was amplified from the *Lactococcus lactis* genome using the oligonucleotides pPAL7-kivDll F and pPAL7-kivDll R. The PCR product was restricted using enzymes HindIII and EcoRI and cloned into the vector pPAL7 restricted by the same restriction enzymes. The resulting vector was named pPAL7-kivDll.

pPAL7-kivDll F (SEQ ID NO 3): ccc AAGCTTtgACTTCTATGTATACCGTGGGTGATTATC with

- a region (italic case) homologous to the sequence of the synthetic gene of the *Lactococcus lactis* kivD gene,
- a region (bold case) harbouring the nucleotides necessary to generate tag-free protein containing a short N-terminal amino acid extension to favour the purification
- a region (underlined case) harbouring the HindIII restriction site pPAL7-kivDll R (SEQ ID NO 4): gGAATTCTTAGCTTTTATTCTGTTCGGCGAACAG with

- a region (italic case) homologous to the sequence of the synthetic gene of the *Lactococcus lactis* kivD gene,
- a region (underlined case) harbouring the EcoRI restriction site The pPAL7-kivDll plasmid was then introduced into the strain BL21 (DE3) competent cells (Invitrogen).

3.2—Overproduction of the Protein KivD

The overproduction of the protein kivD was done applying the same protocol as example #2.2.

3.3—Purification of the Protein KivD

3.3.1—Step 1: Preparation of Cell-Free Extracts

About 188 mg of *E. coli* biomass was suspended in 30 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris was removed by centrifugation at 12000 g for 30 min at 4° C.

3.3.2—Step 2: Affinity Purification

The protein was purified from crude cell-extract by affinity on a Profinity column (BIORAD, Bio-Scale Mini Profinity exact cartridge 5 ml) according to the protocol recommended by the manufacturer. Crude extract was loaded on a 5 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at 4° C. The protein was eluted from the column with 2 column volumes of 100 mM potassium phosphate pH 7.6. The tag remained tightly bound to the resin and the purified protein was released. The fractions containing the protein were pooled and dialyzed against 100 mM potassium phosphate, 150 mM NaCl and 10% glycerol pH 8.

Protein concentration was measured using the Bradford protein assay.

3.4—4-hydroxy-2-ketobutyrate decarboxylase Assay

3.4.1—Chemical Synthesis of 4-hydroxy-2-ketobutyric Acid

Chemical synthesis of 4-hydroxy-2-ketobutyric acid has been described in the publication:

R S Lane; E E Dekker; (1969).2-keto-4-hydroxybutyrate. Synthesis, chemical properties, and as a substrate for lactate dehydrogenase of rabbit muscle Biochemistry., 8(7), 2958-2966.

3.4.2—4-hydroxy-2-ketobutyrate decarboxylase Assay

The decarboxylation of 4-hydroxy-2-ketobutyrate was measured at 30° C. using a coupled enzymatic assay. The 4-hydroxy-2-ketobutyrate decarboxylase activity assay was carried out with 50 mM potassium phosphate buffer pH 6, 0.2 mM NADH, 1 mM MgSO4, 0.5 mM thiamin diphosphate, 72 units/ml alcohol dehydrogenase from *Saccharomyces cerevisiae*, 10 mM 4-hydroxy-2-ketobutyric acid neutralized and about 40 µg of purified protein in a total volume of 1 ml. The consumption of NADH was monitored at 340 nm on a spectrophotometer. The activity detected in control assay, lacking the substrate, was subtracted from the activity detected in the assay with substrate. A unit of 4-hydroxy-2-ketobutyrate decarboxylase activity is the amount of enzyme required to catalyze the decarboxylation of 1 µmol of 4-hydroxy-2-ketobutyric acid per min at 30° C. (Epsilon 340 nm=6290 M-1 cm-1).

3.5—Activity of Purified Enzyme

|  | Activity of purified enzyme (mUI/mg) |
|---|---|
| 4-hydroxy-2-ketobutyrate decarboxylase assay | 147 |

Example 4

Demonstration of the 3-hydroxypropionaldehyde Reductase Activity Encoded by the Gene yqhD of *Escherichia coli*

4.1—Construction of a Strain for YqhD Characterisation: MG1655 ΔyqhD::Km (pTRC99A-yqhD)

4.1.1—Construction of Strain MG1655 ΔyqhD::Km

To delete the yqhD gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used:

ΔyqhDF (SEQ ID NO 5) atgaacaactttaatctgcacac-cccaacccgcattctgtttggtaaag-gcgcaatcgctggtttacgcgaacaaattccgt qtaggctggagctgcttcg with
  a region (lower case) homologous to the sequence (3153377 to 3153456) of the yqhD region (reference sequence on the website www.ecogene.org/),
  a region (upper case) for the amplification of the kanamycin resistance cassette (reference sequence in Datsenko, K. A. & Wanner, B. L., 2000, PNAS, 97: 6640-6645), ΔyqhDR (SEQ ID NO 6) ttagcgggcggcttcgtatatacggcg-gctgacatccaacgtaatgtcat-gattttcgcccagttgggtcatgccgtgctccat atgaatatcctccttag with
  a region (upper case) homologous to the sequence (3154540 to 3154460) of the yqhD region (reference sequence on the website www.ecogene.org/),
  a region (upper case) for the amplification of the kanamycin resistance cassette (reference sequence in Datsenko, K. A. & Wanner, B. L., 2000, PNAS, 97: 6640-6645).

The oligonucleotides ΔyqhDF and ΔyqhDR are used to amplify the kanamycin resistance cassette from the plasmid pKD4. The PCR product obtained is then introduced by electroporation into the strain MG1655 (pKD46). The kanamycin resistant transformants are then selected and the insertion of the resistance cassette is verified by a PCR analysis with the oligonucleotides yqhDF and yqhDR defined below. The strain retained is designated MG1655 ΔyqhD::Km.

yqhDF (SEQ ID NO 7): ggcgtctcgccatacaacaaacgcacatcgggc (homologous to the sequence from 3153068 to 3153100).

yqhDR (SEQ ID NO 8): gggctttgccgacaccttcttcgttcttg (homologous to the sequence from 3154825 to 3154797).

4.1.2—Construction of Plasmid pTRC99A-yqhD

To characterise the YqhD protein, the corresponding gene was expressed from the vector pTRC99A (Amersham).

For this purpose, the yqhD gene was amplified from the *E. coli* genome using the oligonucleotides yqhD F pTRC99A F and yqhD R pTRC99A R. The PCR product was restricted using enzymes HindIII and BspHI and cloned into the vector pTRC99A restricted by the NcoI-HindIII restriction enzymes. The resulting vector was named pTRC99A-yqhD.

yqhD F pTRC99A F (SEQ ID NO 9): cgatgcacgtcatgaa-caactttaatctgcacacccccaacccg, with:
- a region (underlined case) homologous to the sequence (3153377 to 3153408) of the gene yqhD (reference sequence on the website www.ecogene.org/),
- a BspHI restriction site (bold case)

yqhD R pTRC99A R (SEQ ID NO 10): ggcgtaaaaagct-tagcgggcggcttcgtatatacggcg-gctgacatccaacgtaatgtcgtgattttcg with:
- a region (underlined case) homologous to the sequence (3154540 to 3154483) of the gene yqhD (reference sequence on the website www.ecogene.org/),
- a HindIII restriction site (bold case)

The pTRC99A-yqhD plasmid was then introduced into the strain MG 1655 ΔyqhD::Km.

4.2—Overproduction of the Protein YqhD

The protein YqhD was overproduced at 37° C. under aerobic conditions in 2 l baffled Erlenmeyer flasks with 500 ml LB medium with 2.5 g/l glucose and 50 mg/l of ampicillin and 50 mg/l of kanamycin. The flasks were agitated at 200 rpm on an orbital shaker. When the optical density measured at 550 nm reached 0.5 units, the flasks were incubated at 25° C. When the optical density reached 1.2 units, the production of YqhD proteins was induced by adding IPTG to a final concentration of 500 μM. The biomass was harvested by centrifugation when the cultures reached an optical density above 3.5 units. The supernatant was discarded and the pellet was stored at −20° C. before use.

4.3—Purification of the Protein YqhD

4.3.1—Step 1: Preparation of Cell-Free Extracts 400 mg of *E. coli* biomass were suspended in 70 ml of 50 mM Hepes pH 7.5, and a protease inhibitor cocktail. Cells were sonicated on ice (Branson sonifier, 70 W) in a Rosett cell RZ3 during eight cycles of 30 sec with 30 sec intervals. After sonication, cells were incubated for 1 hour at room temperature with 1 mM MgCl2 and 1 UI/ml of DNaseI. Cells debris was removed by centrifugation at 12000 g for 30 min at 4° C. The supernatant was kept as the crude extract.

4.3.2—Step 2: Ammonium Sulphate Precipitation

The crude extract was precipitated at a concentration of 50% ammonium sulphate: solid ammonium sulphate (300 g/l) was added to the crude extract on ice. After 15 min of incubation at 4° C., the mix was centrifuged at 12000 g for 15 min at 4° C. The supernatant was discarded and the precipitate dissolved in 50 ml of 50 mM Hepes pH 7.5, 1 M ammonium sulphate.

4.3.3—Step 3: Hydrophobic Chromatography

Using an Akta Purifier (GE Healthcare), the protein extract from the previous step was loaded onto a 5 ml HiTrap PhenylHP column (GE Healthcare) equilibrated with the same buffer. The column was washed with 10 column volumes of the same buffer. Proteins were eluted with two step gradients, a gradient of 10 column volumes from 1 M to 0.5 M ammonium sulphate and a gradient of 20 column volumes from 0.5 M to 0 M ammonium sulphate. After elution, the column was washed with 10 column volumes of 50 mM Hepes pH 7.5. The flow rate of the column was 2.5 ml/min and 2.5 ml fractions were collected. The fractions which contain the protein were pooled, dialyzed in 50 mM Hepes pH 7.5 and concentrated to a concentration of 1.14 μg/μl.

4.4—3-hydroxypropionaldehyde Reductase Activity Assay 3-hydroxypropionaldehyde reductase activity was assayed by measuring the initial rate of NADPH oxidation with a spectrophotometer at a wavelength of 340 nm and at a constant temperature of 37° C. The reaction mixture using 3-hydroxypropionaldehyde as substrate was carried out in 20 mM Hepes pH 7.5, 0.1 mM Zinc sulphate, 0.2 mM NADPH, 6 μg of purified enzyme in a final volume of 1 ml. The reaction mixture was incubated for 5 min at 37° C. before that the reaction was initiated by the addition of the substrate 3-hydroxypropionaldehyde at a final concentration of 10 mM. The reaction blank contained all components of the reaction mixture except the purified enzyme. One unit of enzyme activity was defined as the amount of enzyme that consumed 1 μmol substrate per minute at 37° C. Specific enzyme activity was expressed as units per mg of protein.

4.5—Activity of Purified Enzyme

|  | Activity of purified enzyme (mUI/mg) |
| --- | --- |
| 3-hydroxypropionaldehyde reductase activity assay | 735 ± 74 |

Example 5

Construction of strains with increased 1.3-propanediol pathway flux and expressing a 4-hydroxy-2-ketobutyrate decarboxylase encoding gene, a 3-hydroxypropionaldehyde reductase encoding gene and a L-homoserine transaminase encoding gene: MG1655 ΔpykF ΔmetA ΔthrLABC (pBBR1MCS5-Ptrc01/RBS01*2-yqhD-kivDll-TT07) (pME101-thrA*1-serC)

5.1—Construction of Strain MG1655 ΔpykF

To delete the pykF gene, the homologous recombination strategy described by Datsenko and Wanner (2000, PNAS, 97: 6640-6645) was used. This strategy allows the insertion of a chloramphenicol or a kanamycin resistance cassette, while deleting most of the genes concerned. For this purpose the following oligonucleotides were used:

ΔpykFF (SEQ ID NO 11) cccatccttctcaacttaaagactaa-gactgtcatgaaaaagaccaaaat-tgtttgcaccatcggaccgaaaaccgaaTGTAG GCTGGAGCT-GCTTCG with
- a region (lower case) homologous to the sequence (1753689-1753766) of the pykF region (reference sequence on the website www.ecogene.org/),
- a region (upper case) for the amplification of the kanamycin resistance cassette, ΔpykFR (SEQ ID NO 12) ggacgtgaacagatgcggtgttagtagt-gccgctcggtaccagtgcaccagaaac-cataactacaacgtcacctttgtgC ATATGAATATCCTCCT-TAG with
- a region (upper case) homologous to the sequence (1755129-1755051) of the pykF region (reference sequence on the website www.ecogene.org/), a region (upper case) for the amplification of the kanamycin resistance cassette.

The oligonucleotides ΔpykFF and ΔpykFR were used to amplify the kanamycin resistance cassette from the plasmid pKD4. The PCR product obtained was then introduced by electroporation into the strain MG1655 (pKD46). The kanamycin resistant transformants were then selected and the insertion of the resistance cassette was verified by a PCR analysis with the oligonucleotides pykFF and pykFR defined below. The strain retained was designated MG1655 ΔpykF::Km.

pykFF (SEQ ID NO 13): gcgtaaccttttccctggaacg (homologous to the sequence from 1753371 to 1753392).

pykFR (SEQ ID NO 14): gcgttgctggagcaacctgccagc (homologous to the sequence from 1755518 to 1755495).

The kanamycin resistance cassette was eliminated. The plasmid pCP20 carrying FLP recombinase acting at the FRT sites of the kanamycin resistance cassette was then introduced into the recombinant sites by electroporation. After a series of cultures at 42° C., the loss of the kanamycin resistance cassettes was verified by a PCR analysis with the same oligonucleotides as used previously (pykFF/pykFR). The strain retained was designated MG1655 ΔpykF.

5.2—Construction of Strain MG1655 ΔpykF ΔmetA

To delete the metA gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used.

ΔmetAF (SEQ ID NO 15): ttcgtgtgccggacgagctacccgccgtcaatttcttgcgtgaa-
gaaaacgtctttgtgatgacaacttctcgtgcgtctTGTAGGCTGGAGCTGCTTCG
with
  a region (lower case) homologous to the sequence (4212310-4212389) of the metA region (reference sequence on the website www.ecogene.org/),
  a region (upper case) for the amplification of the kanamycin resistance cassette (reference sequence in Datsenko, K. A. & Wanner, B. L., 2000, PNAS, 97: 6640-6645),
ΔmetAR (SEQ ID NO 16): atccagcgttggattcatgtgccgtagatcgtatggcgtgatctggtagacg-
taatagttgagccagttggtaaacagtaCATATGAATATCCTCCTTAG
with
  a region (upper case) homologous to the sequence (4213229-4213150) of the metA region (reference sequence on the website www.ecogene.org/),
  a region (upper case) for the amplification of the kanamycin resistance cassette (reference sequence in Datsenko, K. A. & Wanner, B. L., 2000, PNAS, 97: 6640-6645).

The oligonucleotides ΔmetAF and ΔmetAR were used to amplify the kanamycin resistance cassette from the plasmid pKD4. The PCR product obtained was then introduced by electroporation into the strain MG 1655 (pKD46). The kanamycin resistant transformants were then selected and the insertion of the resistance cassette was verified by a PCR analysis with the oligonucleotides metAF and metAR defined below. The strain retained was designated MG1655 ΔmetA::Km.

metAF (SEQ ID NO 17): tcaccttcaacatgcaggctcgacattgg (homologous to the sequence from 4212203 to 4212222).

metAR (SEQ ID NO 18): ataaaaaaggcacccgaaggtgcctgagt (homologous to the sequence from 4213301 to 4213272).

To transfer the ΔmetA::Km, the method of phage P1 transduction was used. The preparation of the phage lysate of the strain MG1655 ΔmetA::Km was used for the transduction into the strain MG1655 ΔpykF.

The kanamycin resistant transformants were then selected and the ΔmetA::Km was verified by a PCR analysis with the previously defined oligonucleotides metF/metAR. The strain retained was designated MG1655 ΔpykF ΔmetA::Km.

The kanamycin resistance cassette was eliminated. The plasmid pCP20 carrying FLP recombinase acting at the FRT sites of the kanamycin resistance cassette was then introduced into the recombinant sites by electroporation. After a series of cultures at 42° C., the loss of the kanamycin resistance cassette was verified by a PCR analysis with the same oligonucleotides as used previously (pykFF/pykFR, and metF/metAR). The strain retained was designated MG1655 ΔpykF ΔmetA.

5.3—Construction of Strain MG1655 ΔpykF ΔmetA ΔthrLABC

To delete the thrLABC operon, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used.

DthrLABF (SEQ ID NO 19): cgggcaatatgtctctgtgtggattaaaaaaagagtgtctgatagcagcttctgaactggttacc
ttcctggctcaccttcgggtgggcctttctggtatacTGTAGGCTGGAGCTGCTTCG
with
  a region (lower case) homologous to the sequence (22-86) of the thrLABC region (reference sequence on the www.ecogene.org/),
  a region (bold underlined lower case) for T7Te transcriptional terminator sequence from T7 phage (Harrington K. J., Laughlin R. B. and Liang S. Proc Natl Acad Sci USA. 2001 Apr. 24; 98(9):5019-24.),
  a region (upper case) for the amplification of the chloramphenicol resistance cassette (reference sequence in Datsenko, K. A. & Wanner, B. L., 2000, PNAS, 97: 6640-6645), DthrLABCR (SEQ ID NO 20): CCCTGTCATTTTTCTCCATAATTTCT-
TCATAAAAAAG CCG G G CTG CATAAAAG CAAA CCCGGCCTGATTGAGATAATGAATAGATT CCCGGGGGAGGCGCCCGCGGATCCC ATATGAATATCCTCCTTAG
with
  a region (upper case) homologous to the sequence (5106-5021) of the thrLABC region (reference sequence on the website www.ecogene.org/),
  a region (italic upper case) for addition of a BamHI-SfoI-SmaI restriction sites
  a region (bold upper case) for the amplification of the chloramphenicol resistance cassette.

The oligonucleotides DthrBF and DthrCR were used to amplify the chloramphenicol resistance cassette from the plasmid pKD3. The PCR product obtained was then introduced by electroporation into the strain MG1655 (pKD46). The chloramphenicol resistant transformants were then selected and the insertion of the resistance cassette was verified by a PCR analysis with the oligonucleotides thrLF and thrCR defined below. The strain retained was designated MG1655 ΔthrLABC::Cm.

thrLF (SEQ ID NO 21): GCCATGCCGCGCTGGTGTTTGGTCGCG (homologous to the sequence from 4639281 to 4639307).

thrCR (SEQ ID NO 22): GCGACCAGAACCAGG-GAAAGTGCG (homologous to the sequence from 5283 to 5260).

To transfer the ΔthrLABC::Cm, the method of phage P1 transduction was used. The preparation of the phage lysate of the strain MG1655 ΔthrLABC::Cm was used for the transduction into the strain MG1655 ΔpykF ΔmetA. The chloramphenicol resistant transformants were then selected and the ΔthrLABC::Cm was verified by a PCR analysis with the previously defined oligonucleotides thrLF and thrCR. The strain retained was designated MG1655 ΔpykF ΔmetA ΔthrLABC::Cm.

The chloramphenicol resistance cassette was eliminated. The plasmid pCP20 carrying FLP recombinase acting at the FRT sites of the chloramphenicol resistance cassettes was then introduced into the recombinant sites by electroporation. After a series of cultures at 42° C., the loss of the chloramphenicol resistance cassette was verified by a PCR analysis with the same oligonucleotides as used previously ((pykFF/pykFR, metAF/metAR, and thrLF/thrCR). The strain retained was designated MG1655 ΔpykF ΔmetA ΔthrLABC.

5.4—Construction of a Plasmid for Overexpression of the L-homoserine Transaminase serC of *Escherichia coli*: pME101-thrA*1-serC Plasmid To increase the expression of the serC gene, the gene was expressed from the pME101-thrA*1 previously described (PCT_WO2008707041) using its proper promoter.

For this purpose, the serC gene was amplified from the *E. coli* genome using the oligonucleotides serC F and serC R. The PCR product was restricted using enzymes XbaI and SmaI and cloned into the vector pME101-thrA*1 restricted by the same restriction enzymes. The resulting vector was named pME101-thrA*1-serC.

serC F (SEQ ID NO 23): TGCTCTAGAGTCCGCGCTGT-GCAAATCCAGAATGG with
a region (upper case) homologous to the sequence (956619-956644) of the gene serC (reference sequence on the website www.ecogene.org/),
a region (bold upper case) harbouring the XbaI site serC R (SEQ ID NO 24): CCCAAGCTTAACTCTCTACAA-CAGAAATAAAAAC with
a region (upper case) homologous to the sequence (958028-958004) of the gene serC region (reference sequence on the website www.ecogene.org/),
a region (bold upper case) harbouring the HindIII site.

The PCR amplified fragment was cut with the restriction enzymes XbaI and HindIII and cloned into the XbaI-HindIII sites of the vector pME101-thrA*1 giving vector pME101-thrA*1-serC.

5.5—Construction of a Plasmid for the Overexpression of the 3-hydroxypropionaldehyde Reductase yqhD Gene of *Escherichia coli* and the 4-hydroxy-2-ketobutyrate decarboxylase kivD Gene of *Lactococcus lactis*: pBBR1MCS5-Ptrc01/RBS01*2-yqhD-kivDll-TT07 plasmid The pME101-yqhD-kivDll-TT07 plasmid was first constructed. The kivDll gene from the pME101-kivDll-TT07 vector (PCT/2009/067994) restricted by BsrBI and BglIII was cloned into the pME101VB01-yqhD vector (previously described in PCT/2007/000509) restricted by SnaBI and BglIII, the resulting plasmid was named pME101-yqhD-kivDll-TT07.

The yqhD and kivDll genes were then PCR amplified from the pME101-yqhD-kivDll-TT07 plasmid with the oligonucleotides Ptrc01-RBS01-yqhD pBBR F and kivD pBBR R. The PCR product was digested with the restriction enzymes SpeI and SmaI and cloned into the vector pBBR1MCS5 (M. E. Kovach, (1995), Gene 166:175-176) restricted by the same enzymes, giving the pBBR1MCS5-Ptrc01/RBS01*2-yqhD-kivDll-TT07 vector.

Ptrc01-RBS01-yqhD pBBR F (SEQ ID NO 25) AgaAC-TAGTgagctgttgacaattaatcatccg-
gctcgtataatgtgtggaagtcgacGGATCC
taaggaggttataaatgaacaacatttaatctgcacacccc
a region (bold upper case) for addition of a SpeI restriction site
a region (bold lower case) for addition of the constitutive Ptrc promoter sequence
a region (italic upper case) for addition of a BamHI restriction site
a region (underlined lower case) for addition of the Ribosome Binding Site sequence
a region (italic lower case) homologous to the sequence (3153377-3153402) of the MG1655 yqhD gene (www.ecogene.org/)

kivD pBBR R (SEQ ID NO 26) GAG*CCCGGG*GCAGAAAGGCCCACCCGAAGGTGAGCCAGTG TGATACGTAGAA TTCTTAATTAAGTTAGCTTTTAT-TCTGTTCGGCG
a region (bold italic upper case) for addition of a SmaI restriction site
a region (underlined upper case) for T7Te transcriptional terminator sequence from T7 phage (Harrington K. J., Laughlin R. B. and Liang S. Proc Natl Acad Sci USA. 2001 Apr. 24; 98(9):5019-24),
a region (bold upper case) for addition of a SnaBI-EcoRI-PacI restriction sites
a region (italic upper case) homologous to the end of the synthetic kivD gene XX Construction of Strain MG1655 ΔpykF ΔmetA ΔthrLABC (pME101-thrA*1-serC) (pBBR1MCS5-Ptrc01/RBS01*2-yqhD-kivDll-TT07)

The pME101-thrA*1-serC and pBBR1MCS5-Ptrc01/RBS01*2-yqhD-kivDll-TT07 plasmids were then introduced into the strain MG1655 ΔmetA ΔpykF ΔthrLABC.

Example 6

Construction of a strain with increased 1.3-propanediol pathway flux on sucrose expressing a 4-hydroxy-2-ketobutyrate decarboxylase encoding gene and a 3-hydroxypropionaldehyde reductase encoding gene, and a sucrose non-PTS transport system: MG1655 ΔpykF ΔmetA ΔthrLABC (pBBR1MCS5-Ptrc01/RBS01*2-yqhD-kivDll-TT07) (pME101-thrA*1-serC) (pKJL101-1)

The pKJL101-1 plasmid was described elsewhere (Jahreis, K. et al. 2002. Adaptation of sucrose metabolism in the *Escherichia coli* wild-type strain EC3132. J. Bact. P5307-5316). The pME101-thrA*1-serC, pBBR1MCS5-Ptrc01/RBS01*2-yqhD-kivDll-TT07 and pKJL101-1 plasmids were introduced into the strain MG1655 ΔmetA ΔpykF ΔthrLABC.

Example 7

Culture for 1,3-propanediol Production

Performances of strains were assessed in 500 ml baffled Erlenmeyer flask cultures using modified M9 medium (Anderson, 1946, Proc. Natl. Acad. Sci. USA 32:120-128) that was supplemented with 4.5 mM threonine, 5 mM methionine, 10 g/l MOPS and 10 g/l sucrose or glucose and adjusted to pH 6.8. Spectinomycin and/or gentamycin were added if necessary at a concentration of 50 mg/l, and/or chloramphenicol was added if necessary at a concentration of 60 mg/l. 100 µM IPTG was also added for induction of the expression vector pME101, if present. A preculture cultivated fro 24 h was used to inoculate a 50 ml culture to an $OD_{600\,nm}$ of about 0.1. The cultures were grown at 37° C. and 200 rpm until the sucrose in the culture medium was exhausted. At this point, remaining sugars and major products were analyzed by HPLC using a Biorad HPX 97H column for separation and a refractometer for detection. Production of 1,3-propanediol was determined by LC/MS/MS.

The performances of different strains are given in table below.

with a P1 phage lysate from strain LJM115 (Jahreis K., Bentler L., Bockmann J., Hans S., Meyer A., Siepelmeyer J., Lengeler J. W. J. Bact. 2002. 184(19):5307-5316).

Chloramphenicol resistant recombinants were selected and the presence of the csc genes was verified by PCR with primers Opg 0590_yfdC seq (SEQ ID N° 27) and Opg 1242_dsdX-dsdA seq (SEQ ID N° 28). The verified and selected strain was called MG1655 ΔRN/yfdC-dsdX::cscB* (Q353H)KAR*::Cm.

Opg 0590_yfdC seq (SEQ ID N° 27): GTGCGGCAAAGAT-TGTGGTG (homologous to the sequence from 2463948 to 2463967)

Opg 1242_dsdX-dsdA seq (SEQ ID N° 28): GCCAGTTTTTCTGCGTGTGCC (homologous to the sequence from 2477624 to 2477604)

| Culture Ref | Strain_ref | Genotype | Carbone source | Growth rate ($h^{-1}$) | [1,3-PDO] (mM) |
|---|---|---|---|---|---|
| FbDI421 | DI0084c02 | MG1655 DpykF DmetA DthrLABC | Glucose | 0.264 | nd |
| FbDI395 | DI0107c01 | MG1655 DpykF DmetA DthrLABC (pME101-thrA*1-serC) (pBBR1MCS5-Ptrc01/RBS01*2-yqhD-kivDll-TT07) | Glucose | 0.171 | 0.30 |
|  | DI0107c01 | MG1655 DpykF DmetA DthrLABC (pME101-thrA*1-serC) (pBBR1MCS5-Ptrc01/RBS01*2-yqhD-kivDll-TT07) | Sucrose | —* | —* |
| FbDI419 | DI0129c01 | MG1655 DpykF DmetA DthrLABC (pME101-thrA*1-serC) (pBBR1MCS5-Ptrc01/RBS01*2-yqhD-kivDll-TT07) (pKJL101.1) | Sucrose | 0.131 | 0.11 |

PDO production of various strains expressing hydroxy keto-acid decarboxylase and 3-hydroxypropionaldehyde reductase cultivated with glucose or sucrose as carbon source;
nd: not detected;
*wildtype E. coli MG1655 does not grow on sucrose carbon source alone.

As can be seen in the table above strains expressing the hydroxy keto-acid decarboxylase and 3-hydroxypropional-dehyde reductase produce PDO from sucrose if the flux for the production of L-homoserine is increased through the deletion of pykF and overexpression of thrA*1, transformation of L-homoserine is reduced by deleting metA and thrABC and transformation of L-homoserine to 4-hydroxy-2-ketobutyrate is catalyzed by the overexpression of serC. To our knowledge no production of PDO has been demonstrated in wild type E. coli on any carbon source, demonstrating that the above modifications convert an E. coli wild type PDO non-producer strain into a PDO producer strain.

Example 8

Construction of Strain: MG1655 ΔpykF ΔmetA Δthr-LABC ΔRN/yfdC-dsdX::cscB*(Q353H)KAR* ΔcscR::Km (pBBR1MCS5-Ptrc01/RBS01*2-yqhD-kivDll-TT07) (pME101-thrA*1-serC)

As can be seen in example 7, the PDO production strain on sucrose (integrating sucrose transport system with pKJL101.1) seems to produce less PDO than the reference strain. We believe this demonstrates a stability problem due to the three different vectors contained in the strain. Thus, we decided to introduce the sucrose transport system on the chromosome in order to obtain a more stable strain.

8.1 Construction of Strain MG1655 ΔRN/yfdC-dsdX::cscB*(Q353H)KAR*::Cm

To construct a strain able to grow on sucrose as sole carbon source, the csc genes were transduced into strain MG1655

8.2 Construction of Strain MG1655 ΔpykF ΔmetA ΔthrLABC ΔRN/yfdC-dsdX::cscB*(Q353H)KAR* ΔcscR::Km To delete the cscR gene, the homologous recombination strategy described by Datsenko & Wanner (2000) was used. This strategy allows the insertion of a chloramphenicol or a kanamycin resistance cassette, while deleting most of the genes concerned. For this purpose the following oligonucleotides were used.

Odi 0195_cscR::Cm F (SEQ ID N° 29) GGTGGAACAACG-GATCAACAGCGGGCAAGGGATCCGCGT-CACTCTTCCCC CTTCACGACCTTCAATAATATG-CAATGCAG<u>TGTAGGCTGGAGCTGCTTCG</u> a region (upper bold case) homologous to the end of the cscR gene, a region (upper underlined case) for the amplification of the kanamycin resistance cassette (reference sequence in Datsenko, K. A. & Wanner, B. L., 2000, PNAS, 97: 6640-6645)

Odi 0196_cscR::Cm R (SEQ ID N° 30) ATGGCTTCAT-TAAAGGATGTCGCACGCCTGGCGGGAGT-GTCGATGATGAC AGTCTCCCGGGTGATGCATAAT-GCAGAATC<u>CATATGAATATCCTCCTTAG</u> a region (upper bold case) homologous to the beginning of the cscR gene, a region (upper underlined case) for the amplification of the kanamycin resistance cassette (reference sequence in Datsenko, K. A. & Wanner, B. L., 2000, PNAS, 97: 6640-6645)

The oligonucleotides Odi 0195_cscR::Cm F and Odi 0196_cscR::Cm R were used to amplify the kanamycin resistance cassette from the plasmid pKD4. The PCR product obtained was then introduced by electroporation into the strain MG1655 ΔRN/yfdC-dsdX::cscB*(Q353H)KAR*::Cm. The kanamycin resistant transformants were then selected and the insertion of the resistance cassette was verified by a PCR analysis with the oligonucleotides Opg 1242_dsdX-dsdA seq described above (SEQ ID N° 28) and Opg 0511_csc8 (SEQ ID N° 31) defined below. The strain retained was designated MG1655 ΔRN/yfdC-dsdX::cscB*(Q353H)KAR*ΔcscR::Km.

Opg 0511_csc8 (SEQ ID N° 31): CGATACATCATCCGTGGAAG (homologous to the sequence of the cscA gene)

To transfer the ΔRN/yfdC-dsdX::cscB*(Q353H)KAR* ΔcscR::Km chromosomal modification, the method of phage P1 transduction was used. The preparation of the phage lysate of the strain MG1655 ΔRN/yfdC-dsdX::cscB*(Q353H) KAR* ΔcscR::Km was used for the transduction into the strain MG1655 ΔpykF ΔmetA ΔthrLABC described in 5.3. The kanamycin resistant transformants were then selected and the ΔRN/yfdC-dsdX::cscB*(Q353H)KAR* ΔcscR::Km was verified by a PCR analysis with the previously defined oligonucleotides Opg 1242_dsdX-dsdA seq/Opg 0511_csc8. The strain retained was designated MG1655 ΔpykF ΔmetA ΔthrLABC ΔRN/yfdC-dsdX::cscB*(Q353H)KAR* ΔcscR::Km.

8.3 Construction of Strain MG1655 ΔpykF ΔmetA ΔthrLABC ΔRN/yfdC-dsdX::cscB*(Q353H)KAR* ΔcscR::Km (pBBR1MCS5-Ptrc01/RBS01*2-yqhD-kivDll-TT07) (pME101-thrA*1-serC)

The pME101-thrA*1-serC and pBBR1MCS5-Ptrc01/RBS01*2-yqhD-kivDll-TT07 plasmids (described in 5.4 and 5.5) were finally introduced into the strain MG1655 ΔmetA ΔpykF ΔthrLABC ΔRN/yfdC-dsdX::cscB*(Q353H)KAR* ΔcscR::Km. The resulting strain was called MG1655 ΔpykF ΔmetA ΔthrLABC ΔRN/yfdC-dsdX::cscB* (Q353 H)KAR * ΔcscR::Km (pBBR1MCS5-Ptrc01/RBS01*2-yqhD-kivDll-TT07) (pME101-thrA*1-serC).

Example 9

Culture of New Production Strain on Sucrose

Strain 1: MG1655 ΔpykF ΔmetA ΔthrLABC (pME101-thrA*1-serC) (pBBR1MCS5-Ptrc01/RBS01*2-yqhD-kivDll-TT07) described in example 5.5;

Strain 2: MG1655 ΔpykF ΔmetA ΔthrLABC ΔRN/yfdC-dsdX::cscB*(Q353H)KAR* ΔcscR::Km (pBBR1MCS5-Ptrc01/RBS01*2-yqhD-kivDll-TT07) (pME101-thrA*1-serC) described in example 8.3.

Production strains were evaluated in small Erlenmeyer flasks using modified M9 medium (Anderson, 1946, Proc. Natl. Acad. Sci. USA 32:120-128) that was supplemented with 4.5 mM threonine, 5 mM methionine and 10 g·L$^{-1}$ MOPS and adjusted to pH 6.8. Glucose was added at a concentration of 10 g·L$^{-1}$ for strain 1 and for strain 2 sucrose at a concentration of 10 g·L$^{-1}$.

A 5 mL preculture was grown at 37° C. for 6.5 hours in a mixed medium (10% LB medium (Sigma 25%) with 2.5 g·L$^{-1}$ glucose or sucrose and 90% minimal medium described above). It was used to inoculate a 50 mL culture to an $OD_{600}$ of 0.1 in minimal medium. IPTG (100 μM) was also added for induction of the expression vector pME101. When necessary, antibiotics were added at concentrations of 50 mg·L$^{-1}$ for kanamycin and spectinomycin and 10 mg·L$^{-1}$ for gentamycin. The temperature of the cultures was 37° C. When the culture had reached an $OD_{600}$ of 7 to 9, extracellular metabolites were analyzed using HPLC with refractometric detection (organic acids and sucrose). Production of 1,3-propanediol was determined by LC/MS/MS. Four repetitions were made for strain 2. Table 2: PDO production in batch culture by strains 1 and 2. SD denotes the standard deviation for the concentration which was calculated on the basis of repetitions. The number of repetitions is indicated in brackets.

| Strain | Carbon source | PDO (mM) | SD | Growth rate (h−1) |
|---|---|---|---|---|
| Strain 1 (N = 14) | Glucose | 0.08 | 0.03 | 0.29 ± 0.02 |
| Strain 2 (N = 4) | Sucrose | 0.12 | 0.02 | 0.32 ± 0.03 |

As can be seen in the table above, PDO production from sucrose as carbon source is in the same range as from glucose as carbon source.

REFERENCES (IN THE ORDER OF CITATION IN THE TEXT)

Schmid K, Schupfner M, Schmitt R (1982), *J. Bacteriol.* 151: 68-76

Schmid K, Ebner R, Altenbuchner J, Sxhmitt R, Lengeler J W (1988), *Mol. Microbiol.* 2: 1-8

Bockmann J, Heuel H, Lengeler J W (1992), *Mol. Gen. Genet.* 235: 22-32

Jahreis K, Bentler L, Bockmann J, Hans S, Meyer A, Siepelmeyer J, Lengeler J W (2002), *J. Bacteriol.* 184: 5307-5316

Tsunekawa H, Azuma S, Okabe M, Okamoto R, Aiba S (1992), *Appl. Environ. Microbiol.* 58 2081-2088

Penfold D W and Macaskie L E (2004), *Biotechnol. Lett.* 26: 1879-1883

Anderson (1946) Proc. Natl. Acad. Sci. USA 32:120-128

The invention claimed is:

1. A method for the fermentative production of 1,3-propanediol from sucrose, comprising the steps of:
culturing a microorganism from the Enterobacteriaceae family genetically modified for the bioproduction of 1,3-propanediol from sucrose on an appropriate culture medium comprising sucrose, wherein the microorganism comprises:
(i) an enzyme having a 2-keto acid decarboxylase activity for decarboxylation of 4-hydroxy-2-ketobutyrate encoded by the kivD gene of *Lactococcus lactis*, and
(ii) an enzyme having hydroxy aldehyde reductase activity encoded by the gene yqhD of *Escherichia coli* for reduction of 3-hydroxypropionaldehyde obtained from decarboxylation of 4-hydroxy-2-ketobutyrate by the 2-keto acid decarboxylase, and
(iii) functional genes coding for a non-PTS sucrose utilization system, enabling the microorganism to utilize sucrose as sole carbon source involving the genes cscBKA from *E. coli*, and
wherein the production of 4-hydroxy-2-ketobutyrate from sucrose is improved in said microorganism by overexpressing a gene encoding homoserine transaminase or homoserine oxidase,
and
recovering 1,3-propanediol from the culture medium.

2. The method of claim 1, wherein the 1,3-propanediol is further purified.

3. A method for the fermentative production of 1,3-propanediol from sucrose, comprising the steps of:
culturing a microorganism from the Enterobacteriaceae family genetically modified for the bioproduction of 1,3-propanediol from sucrose on an appropriate culture medium comprising sucrose, wherein the microorganism comprises:
(i) an enzyme having a 2-keto acid decarboxylase activity for decarboxylation of 4-hydroxy-2-ketobutyrate encoded by the kivD gene of *Lactococcus lactis*, and
(ii) an enzyme having hydroxy aldehyde reductase activity encoded by the gene yqhD of *Escherichia coli* for reduction of 3-hydroxypropionaldehyde obtained from decarboxylation of 4-hydroxy-2-ketobutyrate by the 2-keto acid decarboxylase, and
(iii) functional genes coding for a PTS sucrose utilization system and/or for a non-PTS sucrose utilization system, enabling the microorganism to utilize sucrose as sole carbon source, chosen among scrKYAB from *Salmonella* or cscBKA from *E. coli*, and
wherein the production of 4-hydroxy-2-ketobutyrate from sucrose is improved in said microorganism by overexpressing a gene encoding homoserine transaminase or homoserine oxidase,
and
recovering 1,3-propanediol from the culture medium.

4. The method of claim 3, wherein said functional genes code for a PTS sucrose utilization system.

5. The method of claim 3, wherein the functional gene is scrKYAB from *Salmonella*.

* * * * *

SEQUENCE LISTING

<160> NUMBER OF SEQ ID NOS: 31

<210> SEQ ID NO 1
<211> LENGTH: 40
<212> TYPE: DNA
<213> ORGANISM: Artificial Sequence
<220> FEATURE:
<223> OTHER INFORMATION: Oligonucleotide

<400> SEQUENCE: 1
cccaagcttt gatggctcaa atcttcaatt ttagttctgg                          40

<210> SEQ ID NO 2
<211> LENGTH: 35
<212> TYPE: DNA
<213> ORGANISM: Artificial Sequence
<220> FEATURE:
<223> OTHER INFORMATION: Oligonucleotide

<400> SEQUENCE: 2
ggaattctta accgtgacgg cgttcgaact caacc                              35

<210> SEQ ID NO 3
<211> LENGTH: 39
<212> TYPE: DNA
<213> ORGANISM: Artificial Sequence
<220> FEATURE:
<223> OTHER INFORMATION: Oligonucleotide

<400> SEQUENCE: 3
cccaagcttt gacttctatg tataccgtgg gtgattatc                           39

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide

<400> SEQUENCE: 4
ggaattctta gcttttattc tgttcggcga acag                               34

<210> SEQ ID NO 5
<211> LENGTH: 101
<212> TYPE: DNA
<213> ORGANISM: Artificial Sequence
<220> FEATURE:
<223> OTHER INFORMATION: Oligonucleotide

<400> SEQUENCE: 5
atgaacaact ttaatctgca caccccaacc cgcattctgt ttggtaaagg cgcaatcgct    60
ggtttacgcg aacaaattcc gtgtaggctg gagctgcttc g                       101

<210> SEQ ID NO 6
<211> LENGTH: 101
<212> TYPE: DNA
<213> ORGANISM: Artificial Sequence
<220> FEATURE:
<223> OTHER INFORMATION: Oligonucleotide

<400> SEQUENCE: 6
ttagcgggcg gcttcgtata tacggcggct gacatccaac gtaatgtcat gattttcgcc    60
cagttgggtc atgccgtgct ccatatgaat atcctcctta g                       101

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide

<400> SEQUENCE: 7
ggcgtctcgc catacaacaa acgcacatcg ggc                                33

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide

<400> SEQUENCE: 8
gggctttgcc gacaccttct tcgttcttg                                    29

<210> SEQ ID NO 9
<211> LENGTH: 43
<212> TYPE: DNA
<213> ORGANISM: Artificial Sequence
<220> FEATURE:
<223> OTHER INFORMATION: Oligonucleotide

<400> SEQUENCE: 9
cgatgcacgt catgaacaac tttaatctgc acaccccaac ccg                    43

<210> SEQ ID NO 10
<211> LENGTH: 70
<212> TYPE: DNA
<213> ORGANISM: Artificial Sequence
<220> FEATURE:
<223> OTHER INFORMATION: Oligonucleotide

<400> SEQUENCE: 10
ggcgtaaaaa gcttagcggg cggcttcgta tatacggcgg ctgacatcca acgtaatgtc  60
gtgattttcg                                                         70

<210> SEQ ID NO 11
<211> LENGTH: 98
<212> TYPE: DNA
<213> ORGANISM: Artificial Sequence
<220> FEATURE:
<223> OTHER INFORMATION: Oligonucleotide

<400> SEQUENCE: 11
cccatccttc tcaacttaaa gactaagact gtcatgaaaa agaccaaaat tgtttgcacc  60
atcggaccga aaccgaatg taggctggag ctgcttcg                           98

<210> SEQ ID NO 12
<211> LENGTH: 99
<212> TYPE: DNA
<213> ORGANISM: Artificial Sequence
<220> FEATURE:
<223> OTHER INFORMATION: Oligonucleotide

<400> SEQUENCE: 12
ggacgtgaac agatgcggtg ttagtagtgc cgctcggtac cagtgcacca gaaaccataa  60
ctacaacgtc acctttgtgc atatgaatat cctccttag                         99

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
gcgtaacctt ttccctggaa cg                                           22

```
<210> SEQ ID NO 14
<211> LENGTH: 24
<212> TYPE: DNA
<213> ORGANISM: Artificial Sequence
<220> FEATURE:
<223> OTHER INFORMATION: Oligonucleotide

<400> SEQUENCE: 14
gcgttgctgg agcaacctgc cagc                                              24

<210> SEQ ID NO 15
<211> LENGTH: 100
<212> TYPE: DNA
<213> ORGANISM: Artificial Sequence
<220> FEATURE:
<223> OTHER INFORMATION: Oligonucleotide

<400> SEQUENCE: 15
ttcgtgtgcc ggacgagcta cccgccgtca atttcttgcg tgaagaaaac gtctttgtga       60
tgacaacttc tcgtgcgtct tgtaggctgg agctgcttcg                            100

<210> SEQ ID NO 16
<211> LENGTH: 100
<212> TYPE: DNA
<213> ORGANISM: Artificial Sequence
<220> FEATURE:
<223> OTHER INFORMATION: Oligonucleotide

<400> SEQUENCE: 16
atccagcgtt ggattcatgt gccgtagatc gtatggcgtg atctggtaga cgtaatagtt       60
gagccagttg gtaaacagta catatgaata tcctccttag                            100

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide

<400> SEQUENCE: 17
tcaccttcaa catgcaggct cgacattggc                                        30

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide

<400> SEQUENCE: 18
ataaaaaagg cacccgaagg tgcctgaggt                                        30

<210> SEQ ID NO 19
<211> LENGTH: 122
<212> TYPE: DNA
<213> ORGANISM: Artificial Sequence
<220> FEATURE:
<223> OTHER INFORMATION: Oligonucleotide

<400> SEQUENCE: 19
cgggcaatat gtctctgtgt ggattaaaaa aagagtgtct gatagcagct tctgaactgg       60
ttaccttcct ggctcacctt cgggtgggcc tttctggtat actgtaggct ggagctgctt      120
cg                                                                    122
```

<210> SEQ ID NO 20
<211> LENGTH: 130
<212> TYPE: DNA
<213> ORGANISM: Artificial Sequence
<220> FEATURE:
<223> OTHER INFORMATION: Oligonucleotide

<400> SEQUENCE: 20
ccctgtcatt tttctccata atttcttcat aaaaaagccg ggctgcataa aagcaaaccc    60
ggcctgattg agataatgaa tagattcccg ggggaggcgc cgcggatcc catatgaata   120 tcctccttag                                                         130

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide

<400> SEQUENCE: 21
gccatgccgc gctggtgttt ggtcgcg                                       27

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide

<400> SEQUENCE: 22
gcgaccagaa ccagggaaag tgcg                                          24

<210> SEQ ID NO 23
<211> LENGTH: 35
<212> TYPE: DNA
<213> ORGANISM: Artificial Sequence
<220> FEATURE:
<223> OTHER INFORMATION: Oligonucleotide

<400> SEQUENCE: 23
tgctctagag tccgcgctgt gcaaatccag aatgg                              35

<210> SEQ ID NO 24
<211> LENGTH: 34
<212> TYPE: DNA
<213> ORGANISM: Artificial Sequence
<220> FEATURE:
<223> OTHER INFORMATION: Oligonucleotide

<400> SEQUENCE: 24
cccaagctta actctctaca acagaaataa aaac                               34

<210> SEQ ID NO 25
<211> LENGTH: 104
<212> TYPE: DNA
<213> ORGANISM: Artificial Sequence
<220> FEATURE:
<223> OTHER INFORMATION: Oligonucleotide

<400> SEQUENCE: 25
agaactagtg agctgttgac aattaatcat ccggctcgta taatgtgtgg aagtcgacgg    60
atcctaagga ggttataaat gaacaacttt aatctgcaca cccc                   104

```
<210> SEQ ID NO 26
<211> LENGTH: 86
<212> TYPE: DNA
<213> ORGANISM: Artificial Sequence
<220> FEATURE:
<223> OTHER INFORMATION: Oligonucleotide

<400> SEQUENCE: 26
gagcccgggg cagaaaggcc cacccgaagg tgagccagtg tgatacgtag aattcttaat    60
taagttagct tttattctgt tcggcg                                         86

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
gtgcggcaaa gattgtggtg                                                20

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide

<400> SEQUENCE: 28
gccagttttt ctgcgtgtgc c                                              21

<210> SEQ ID NO 29
<211> LENGTH: 100
<212> TYPE: DNA
<213> ORGANISM: Artificial Sequence
<220> FEATURE:
<223> OTHER INFORMATION: Oligonucleotide

<400> SEQUENCE: 29
ggtggaacaa cggatcaaca gcgggcaagg gatccgcgtc actcttcccc cttcacgacc    60
ttcaataata tgcaatgcag tgtaggctgg agctgcttcg                         100

<210> SEQ ID NO 30
<211> LENGTH: 100
<212> TYPE: DNA
<213> ORGANISM: Artificial Sequence
<220> FEATURE:
<223> OTHER INFORMATION: Oligonucleotide

<400> SEQUENCE: 30
atggcttcat taaaggatgt cgcacgcctg gcgggagtgt cgatgatgac agtctcccgg    60
gtgatgcata atgcagaatc catatgaata tcctccttag                         100

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
cgatacatca tccgtggaag                                                20
```